United States Patent
Garcia et al.

(10) Patent No.: US 7,217,429 B2
(45) Date of Patent: May 15, 2007

(54) TABLETED ORAL PHARMACEUTICAL DOSAGE FORM, WITH ENTERIC COATING, CONTAINING A COMPOUND OF BENZIMIDAZOLE LABILE IN AN ACID MEDIUM

(76) Inventors: Javier Lizcano Garcia, Avda. Mare de Deu de Montserrat, 221, 08041 Barcelona (ES); Jaume Sangra Perez, Avda. Mare de Deu de Montserrat, 221, 08041 Barcelona (ES); Pere Joan Solanas Ibarra, Avda. Mare de Deu de Montserrat, 221, 08041 Barcelona (ES); Antonio Lopez Cabrera, Avda. Mare de Deu de Montserrat, 221, 08041 Barcelona (ES)

( * ) Notice: Subject to any disclaimer, the term of this patent is extended or adjusted under 35 U.S.C. 154(b) by 0 days.

(21) Appl. No.: 10/317,702

(22) Filed: Dec. 12, 2002

(65) Prior Publication Data

US 2003/0118650 A1 Jun. 26, 2003

(30) Foreign Application Priority Data

Dec. 18, 2001 (ES) ................................ 200102820

(51) Int. Cl.
*A61K 9/26* (2006.01)
*A61K 9/24* (2006.01)

(52) U.S. Cl. .................. 424/470; 424/469; 424/472; 424/474

(58) Field of Classification Search ............... 424/468, 424/475, 479, 480, 439, 449, 464, 469, 474
See application file for complete search history.

(56) References Cited

U.S. PATENT DOCUMENTS 4,786,505 A * 11/1988 Lovgren et al. ............ 424/468

FOREIGN PATENT DOCUMENTS

| EP | 0 244 380 | 1/1993 |
|---|---|---|
| EP | 0 773 025 | 6/2000 |
| WO | 96/01623 | 1/1996 |
| WO | WO 9601623 A1 * | 1/1996 |

* cited by examiner

*Primary Examiner*—Michael G. Hartley
*Assistant Examiner*—Micah-Paul Young
(74) *Attorney, Agent, or Firm*—Norris McLaughlin & Marcus PA

(57) ABSTRACT

The pharmaceutical dosage form consists of a plurality of units containing a benzimidazole compound labile in an acid medium as the active principle, each unit being comprised of an inert core, a layer containing the active principle and an intermediate layer. These units, mixed with compression excipients, compressed and coated with an enteric coating, provide a tableted pharmaceutical dosage form suitable for oral administration for preventing and treating disorders related to abnormal secretion of gastric acid.

8 Claims, No Drawings

TABLETED ORAL PHARMACEUTICAL DOSAGE FORM, WITH ENTERIC COATING, CONTAINING A COMPOUND OF BENZIMIDAZOLE LABILE IN AN ACID MEDIUM

FIELD OF THE INVENTION

The invention relates to new tableted pharmaceutical dosage forms, with an enteric coating, consisting of a plurality of units containing a compound of benzimidazole labile in an acid medium, suitable for oral administration. The invention also relates to the process for preparing said pharmaceutical dosage forms and to their use in human and animal health care.

BACKGROUND OF THE INVENTION

Omeprazole, 5-methoxy-2-[[(4-methoxy-3,5-dimethyl-2-pyridyl) methyl]sulphinyl]-1H-benzimidazole, is a compound of benzimidazole that can inhibit gastric secretion in mammals, so that it is useful for preventing and treating disorders related to secretion of gastric acid, such as gastric ulcers, duodenal ulcers, reflux oesophagitis, Zolliger-Ellison syndrome, etc. Other benzimidazole compounds with anti-ulcerous activity are pantoprazole, lansoprazole and rabeprazole.

Omeprazole, as other benzimidazole compounds of therapeutic interest, is labile in an acid medium, which creates a great number of problems when developing a pharmaceutical form meant for oral administration as said compound breaks down upon contact with the stomach contents, a strongly acidic medium. Its labile nature may be responsible for the variability in the intra- and inter-individual therapeutic response of omeprazole.

To prevent contact between compounds labile in an acid medium and gastric juice after oral administration of said compounds, solid pharmaceutical forms have been developed that are comprised of a core containing the compound labile in an acid medium and an outer layer that provides a gastro-resistant coating, which can be separated by one or more intermediate layers. In certain cases it is not possible to use conventional enteric coatings of acidic nature as the active compound would break down upon direct or indirect contact with said coating, as made manifest by a change in color and a degradation of the active compound over time.

There exist several ways of solving the problem of stability of the active compound. One of them consists of creating an alkaline environment around the benzimidazole compound labile in an acid medium, which is achieved by means of alkali salts of the benzimidazole compound and/or by incorporating an alkaline reacting compound in the gastro-resistant pharmaceutical preparation [see, for example, European Patent Application EP 0 244 380 and U.S. Pat. No. 4,786,505]. Another way of solving the problem of stability of the active compound is the creation of a physical barrier that manages to separate completely the active compound and the enteric layer, thereby preventing any degradation of the active compound, and involves the use of pharmaceutically acceptable excipients with the exception of those giving an alkaline reaction [see, for example, European Patent EP 0 773 025].

Patent application WO 96/01623 describes a multiple unit tableted dosage form containing omeprazole or an alkali salt thereof, consisting of units arranged in layers that contain the active compound individually coated with an enteric coating. Such units arranged as enteric coated layers are mixed with excipients for tablets and are tableted together.

SUMMARY OF THE INVENTION

The invention addresses the problem of developing new pharmaceutical dosage forms, enteric coated, for oral administration, meant to increase the number of available means for effective administration of benzimidazole compounds labile in an acid medium.

The solution provided by this invention is based on the inventors' observation that tableted oral pharmaceutical dosage forms with enteric coating consisting of multiple units containing a benzimidazole compound labile in an acid medium are stable and useful for effective administration of benzimidazole compounds labile in an acid medium.

DETAILED DESCRIPTION OF THE INVENTION

The invention provides a tableted pharmaceutical oral dosage form, with an enteric coating, consisting of a plurality of units containing a compound of benzimidazole labile in an acid medium as the active principle, hereinafter referred to as the dosage form of the invention, comprised of:

(a) A plurality of units containing a benzimidazole compound labile in an acid medium as the active principle that contain:
  i) an inert core;
  ii) an active layer deposited on said inert core i), formed by a benzimidazole compound labile in an acid medium, a non-alkaline water-soluble inert polymer and one or more pharmaceutically acceptable inert excipients; and
  iii) an intermediate layer consisting of an inert non-alkaline coating formed by a non-alkaline, water-soluble inert polymer and one or more pharmaceutically acceptable inert excipients, with said intermediate layer being disposed over the aforementioned active layer ii) that covers the inert core i);

(b) one or more pharmaceutically acceptable inert excipients, of which one or more are compression excipients; and (c) an enteric coating layer that coats said plurality of units containing a benzimidazole compound labile in an acid medium as the active principle and said pharmaceutically acceptable inert excipients (b).

In the sense used in this description, the term "benzimidazole compound labile in an acid medium" includes benzimidazole compounds of therapeutic interest with a half-life under 10 minutes in an aqueous solution of pH less than 4, and/or a half-life between 10 minutes and 65 hours in an aqueous solution with a pH of 7, such as for example omeprazole, lansoprazole, pantoprazole and rabeprazole or their corresponding enantiomers.

In a specific embodiment, said benzimidazole compound labile in an acid medium is a compound of 2-[[(2-pyridyl) methylsulphinyl]benzimidazole with the formula (I) or its enantiomers

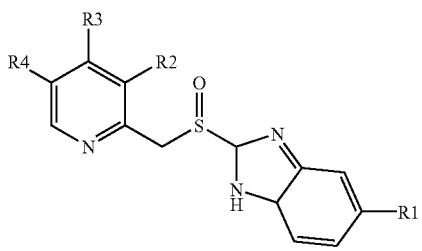

where
- $R^1$ is hydrogen, methoxy or difluoromethoxy,
- $R^2$ is methyl or methoxy,
- $R^3$ is methoxy, 2,2,2-trifluoroethoxy or 3-methoxypropoxy, and
- $R^4$ is hydrogen or methyl.

The inert core (i) is a pharmaceutically inert substance with relation to the active principle. That is, it does not react with the active principle under the conditions used to cause its decomposition, and may consist of a sugar, such as saccharose, starch and the mixtures thereof. In a specific embodiment, said inert cores consist of a mixture of saccharose and corn starch, and have an average grain size of between 0.25 and 1.4 mm and meet the requirements of the USP (United States Pharmacopoeia) [Monograph on Sugar Spheres, USP NF 18]. In a specific embodiment, the inert cores (i) are present in the unit comprising the dosage form of the invention in an amount between 5% and 35% by weight with respect to the total weight of the unit.

The active layer (ii) is comprised of a benzimidazole compound labile in an acid medium, preferably a compound of formula (I), for example, omeprazole or one of its individual R or S enantiomers, a non-alkaline, water-soluble inert polymer such as hydroxypropylmethyl cellulose (HPMC) or hydroxypropyl cellulose (HPC). In the sense used in this description the term "inert" applied to a polymer or excipient indicates that said compound does not react under the conditions used. In a particular embodiment, the active layer (ii) is present in the unit comprising the dosage form of the invention in an amount between 1.6% and 35% by weight with respect to the total weight of the unit.

The intermediate layer (iii) comprises an inert non-alkaline coating consisting of an inert, non-alkaline water-soluble polymer such as HPMC or HPC, and one or more pharmaceutically acceptable inert excipients, such as a pigment, for example titanium dioxide. In a specific embodiment, the intermediate layer (iii) is present in the unit comprising the dosage form of the invention in an amount between 0.5% and 15% by weight with respect to the total weight of the unit.

The dosage form of the invention additionally comprises one or more pharmaceutically acceptable inert excipients of which one or more are compression excipients, such as dilutants, for example microcrystalline cellulose, solubilisers, for example, crospovidone, and lubricants, for example, magnesium stearate. In a specific embodiment said compression excipients are present in the dosage form of the invention in an amount between 40% and 80% by weight with respect to the total weight of the dosage form.

The outer layer of the dosage form of the invention comprises an enteric coating that includes a gastro-resistant polymer, such as a methacrylic copolymer, for example a copolymer formed by methacrylic acid and esters of methacrylic acid, a plasticiser such as triethyl acetate or the like, and one or more pharmaceutically acceptable inert excipients, such as talcum. In a specific embodiment, said outer enteric coating is present in the dosage form of the invention in an amount between 4% and 30% by weight with respect to the total weight of the dosage form. The outer layer of the dosage form of the invention can contain, in addition, a colored coating comprising a mixture of colorants and opacifiers together with other pharmaceutically acceptable excipients, such as a mixture of polydextrose, HPMC, titanium dioxide, PEG 400 and colorants. The colored coating layer can be mixed with the outer enteric coating layer to define a single outer layer. In a specific embodiment, said colored layer is present in the dosage form of the invention in an amount between 1.5% and 15% by weight with respect to the total weight of the dosage form.

The units containing a benzimidazole compound labile in an acid medium as the active principle can be obtained by conventional techniques. A review of the various techniques for preparing said units with therapeutic applications can be found in the book *Pharmaceutical Pelletization Technology*, published by Isaac Ghebre-Sellassie, Marcel Dekker, Inc., 1989. In a specific embodiment, said units are obtained applying the various layers with conventional fluidised bed coating techniques, using aqueous solutions or suspensions of the components of said layers. In short, in a fluidised bed apparatus the inert cores are covered with a first layer containing the benzimidazole compound labile in an acid medium and a non-alkaline, water-soluble inert polymer, such as HPMC or HPC. Afterwards said active layer is covered with an intermediate layer containing a non-alkaline inert coating formed by a non-alkaline, water-soluble inert polymer, such as HPMC or HPC, and one or more pharmaceutically acceptable inert excipients, for example a pigment such as titanium dioxide.

The dosage form of the invention can be obtained by conventional techniques by a process that involves mixing a plurality of units containing a benzimidazole compound labile in an acid medium as an active principle with one or more compression excipients, and compressing the resulting mixture. Compression can be effected by methods with dry or wet routes. A review of the various methods for preparing tablets is mentioned, for example, in the *Tratado de Farmacia Galénica (Treatise of Gallenic Pharmacy)*, C. Faulí i Trillo, Luzán 5, S. A. de Ediciones (1993), Chapter 36, pages 521–541.

The active principles can be administered in the same doses and with the same protocols as those of the commercially available pharmaceutical forms. In general, the dose of active principle is between approximately 5 mg/day and 100 mg/day, adjusted to the individual needs of the patient and according to the specialist's considerations.

The dosage form of the invention is resistant to solution in an acid medium, stable in its passage through the gastric juice and allows liberating the active principle in an alkaline or neutral aqueous medium, the characteristic conditions of the proximal area of the small intestine.

The invention also provides a method for preventing and treating disorders related to abnormal secretion of gastric acid, comprising administering a therapeutically affective amount of the dosage form of the invention to a patient affected by the abnormal secretion of gastric acid.

The following example is shown by way of illustration of the invention, and should not be understood as limiting its scope.

EXAMPLE

Enteric Tablets Comprising Multiple Units Containing Omeprazole

A suspension of the active principle is prepared dispersing 1,250 g of the active principle [omeprazole or lansoprazole] and 478.73 g of HPMC in 4,033 g of purified (deionised) water.

In a fluidised bed apparatus are introduced 2,791.69 g of inert cores, spherical, of uniform size 0.25–0.355 mm of saccharose, over which the suspension obtained previously is sprayed.

In 2,855.5 g of purified water are dispersed 427.26 g of HPMC and 56.83 g of titanium dioxide and the resulting aqueous suspension is sprayed over the spheres obtained previously. After spraying and before applying the next layer the spheres thus obtained are dried.

Then 1,988 g of said spheres are mixed with 4,783.7 g of microcrystalline cellulose, 403.4 g of crospovidone and 24.8 g of magnesium stearate and compressed.

In 331.04 g of purified water are dispersed 33.104 g of a mixture of polydextrose, HPMC, titanium dioxide, PEG 400 and colorants E110/E124/E132 and the resulting suspension is scattered over 800 g of the previously obtained tablets. After spraying and before applying the next layer the spheres thus obtained are dried.

In 170.67 g of purified water are scattered 176.28 g of copolymer of methacrylic acid—ethyl acrylate of USP/Ph.Eur. quality, 7.4 g of triethyl citrate and 5.31 g of talcum, and the resulting aqueous suspension is sprayed over the tablets coated with the colored layer previously obtained. After spraying and applying this enteric coating layer the resulting tablets, with an enteric coating layer, are dried.

The invention claimed is:

1. A tableted oral pharmaceutical dosage form, covered with an enteric coating, consisting of a plurality of units that contain a benzimidazole compound labile in an acid medium as the active principle, comprising:
    (a) a plurality of units containing a benzimidazole compound labile in an acid medium as the active principle that contain:
        i) an inert core;
        ii) an active layer deposited on said inert core i), formed by a benzimidazole compound labile in an acid medium, a non-alkaline water-soluble inert polymer and one or more pharmaceutically acceptable inert excipients; and
        iii) an intermediate layer consisting of an inert non-alkaline coating formed by a non-alkaline, water-soluble inert polymer and one or more pharmaceutically acceptable inert excipients, with said intermediate layer being disposed over the aforementioned active layer ii) that covers the inert core i);
    (b) one or more pharmaceutically acceptable inert excipients, of which one or more are compression excipients; and
    (c) an enteric coating layer that coats the tableted oral pharmaceutical dosage form
    wherein each of the plurality of units is provided without an individual enteric coating layer.

2. Tableted oral pharmaceutical dosage form according to claim 1, wherein said benzimidazole compound labile in an acid medium is a compound of 2-[(2-pyridyl) methylsulphinyl] benzimidazole of formula (I) or its enantiomers

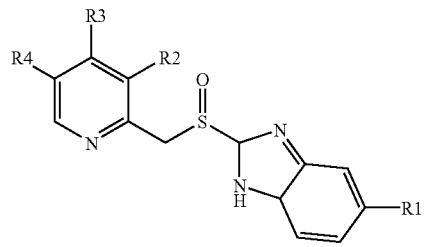

(I)

where
    $R^1$ is hydrogen, methoxy or difluoromethoxy,
    $R^2$ is methyl or methoxy,
    $R^3$ is methoxy, 2,2,2-trifluoroethoxy or 3-methoxypropoxy, and
    $R^4$ is hydrogen or methyl.

3. Tableted oral pharmaceutical dosage form according to claim 1, wherein said benzimidazole compound labile in an acid medium is selected from the group consisting of omeprazole, lansoprazole, rabeprazole and pantoprazole or their corresponding enantiomers.

4. Tableted oral pharmaceutical dosage form according to claim 1, wherein said non-alkaline, water-soluble inert polymer present in the active layer ii) is selected from among hydroxypropylmethyl cellulose (HPMC) and hydroxypropyl cellulose (HPC).

5. Tableted oral pharmaceutical, dosage form according to claim 1, wherein said non-alkaline, water-soluble inert polymer present in the intermediate layer iii) is hydroxypropylmethyl cellulose (HPMC).

6. Tableted oral pharmaceutical dosage form according to claim 1, wherein said compression excipients are selected from among the group formed by dilutants, disintegrators, lubricants and their mixtures.

7. Tableted oral pharmaceutical dosage form according to claim 1, wherein said enteric coating layer (c) that covers the aforementioned tableted oral pharmaceutical dosage form, comprises a gastro-resistant polymer, a plasticiser and one or more pharmaceutically acceptable inert excipients.

8. A process for preparing a tableted oral pharmaceutical dosage form, covered by an enteric coating, consisting of multiple units containing a benzimidazole compound labile in an acid medium as the active principle, according to claim 1, involving:
    applying on an inert core an aqueous suspension of a benzimidazole compound labile in an acid medium, a non-alkaline, water-soluble inert polymer, and one or more pharmaceutically acceptable inert excipients to obtain an active later that coats the inert core,
    applying on said active layer an intermediate layer containing a non-alkaline inert coating consisting of a non-alkaline, water-soluble inert polymer and one or more pharmaceutically acceptable inert excipients to obtain a unit containing a benzimidazole compound labile in an acid medium as the active principle;
    mixing a plurality of said units containing a benzimidazole compound labile in an acid medium as the active principle with one or more pharmaceutically acceptable inert excipients, of which one or more are compression excipients, and compressing said mixture to obtain a tablet, wherein each of the plurality of units are provided for mixing without an individual enteric coating layer; and
    covering said tablet with an aqueous suspension comprised of a gastro-resistant polymer, a plasticiser and one or more pharmaceutically acceptable inert excipients to form an outer enteric coating.

* * * * *